United States Patent
Lau et al.

(10) Patent No.: US 7,953,809 B2
(45) Date of Patent: *May 31, 2011

(54) METHOD AND SYSTEM FOR ENHANCED MESSAGING

(75) Inventors: Chung Lau, Sunnyvale, CA (US); C. Douglass Thomas, Campbell, CA (US)

(73) Assignee: IpVenture, Inc., Los Altos, CA (US)

(*) Notice: Subject to any disclaimer, the term of this patent is extended or adjusted under 35 U.S.C. 154(b) by 408 days.

This patent is subject to a terminal disclaimer.

(21) Appl. No.: 12/214,434

(22) Filed: Jun. 19, 2008

(65) Prior Publication Data

US 2008/0261636 A1   Oct. 23, 2008

Related U.S. Application Data

(63) Continuation of application No. 10/397,474, filed on Mar. 26, 2003, now Pat. No. 7,403,972.

(60) Provisional application No. 60/444,198, filed on Jan. 30, 2003, provisional application No. 60/418,491, filed on Oct. 15, 2002, provisional application No. 60/404,645, filed on Aug. 19, 2002, provisional application No. 60/375,998, filed on Apr. 24, 2002.

(51) Int. Cl.
G06F 15/16 (2006.01)
G06F 12/00 (2006.01)

(52) U.S. Cl. ......................... 709/206; 709/207

(58) Field of Classification Search .......... 709/217–218, 709/206–207, 226–229, 250
See application file for complete search history.

(56) References Cited

U.S. PATENT DOCUMENTS

| | | |
|---|---|---|
| 5,389,934 A | 2/1995 | Kass |
| 5,400,020 A | 3/1995 | Jones et al. |
| 5,461,365 A | 10/1995 | Schlager et al. |
| 5,491,486 A | 2/1996 | Welles, II et al. |
| 5,512,902 A | 4/1996 | Guthrie et al. |
| 5,515,858 A | 5/1996 | Myllymaki |
| 5,528,247 A | 6/1996 | Nonami |
| 5,528,518 A | 6/1996 | Bradshaw et al. |
| 5,539,748 A | 7/1996 | Raith |
| 5,541,845 A | 7/1996 | Klein |
| 5,550,551 A | 8/1996 | Alesio |
| 5,568,119 A | 10/1996 | Schipper et al. |
| 5,570,412 A | 10/1996 | LeBlanc |
| 5,576,716 A | 11/1996 | Sadler |

(Continued)

FOREIGN PATENT DOCUMENTS

EP   0 874 529 A2 * 10/1998

(Continued)

OTHER PUBLICATIONS

Office Action for U.S. Appl. No. 10/397,474, dated Aug. 23, 2006.

(Continued)

*Primary Examiner* — Zarni Maung

(57) ABSTRACT

Techniques for acquiring, sending, receiving or using status information from a remote location over a network are disclosed. The status information is transmitted over the network between or among electronic devices. The status information can be provided by one or more sensors associated with the electronic device that is transmitting the status information. The status information can be transmitted with messages so as to enhance the messages. The electronic devices include at least computing devices, such as personal computers, personal digital assistants, pagers, and mobile telephones.

25 Claims, 7 Drawing Sheets

U.S. PATENT DOCUMENTS

| | | |
|---|---|---|
| 5,592,173 A | 1/1997 | Lau et al. |
| 5,598,460 A | 1/1997 | Tendler |
| 5,604,708 A | 2/1997 | Helms et al. |
| 5,623,260 A | 4/1997 | Jones |
| 5,629,678 A | 5/1997 | Gargano et al. |
| 5,652,570 A | 7/1997 | Lepkofker |
| 5,673,692 A | 10/1997 | Schulze et al. |
| 5,710,551 A | 1/1998 | Ridgeway |
| 5,712,619 A | 1/1998 | Simkin |
| 5,731,757 A | 3/1998 | Layson et al. |
| 5,731,788 A | 3/1998 | Reeds |
| 5,742,233 A | 4/1998 | Hoffman et al. |
| 5,751,245 A | 5/1998 | Janky et al. |
| 5,771,001 A | 6/1998 | Cobb |
| 5,774,876 A | 6/1998 | Woolley et al. |
| 5,797,091 A | 8/1998 | Clise et al. |
| RE35,920 E * | 10/1998 | Sorden et al. |
| 5,826,195 A | 10/1998 | Westerlage et al. |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,861,841 A | 1/1999 | Gildea et al. |
| 5,883,594 A | 3/1999 | Lau |
| 5,889,770 A | 3/1999 | Jokiaho et al. |
| 5,905,461 A | 5/1999 | Neher |
| 5,913,078 A | 6/1999 | Kimura et al. |
| 5,948,043 A | 9/1999 | Mathis |
| 5,959,575 A | 9/1999 | Abbott |
| 5,959,577 A | 9/1999 | Fan et al. |
| 5,963,130 A | 10/1999 | Schlager et al. |
| 5,982,285 A | 11/1999 | Bueche et al. |
| 5,991,690 A | 11/1999 | Murphy |
| 5,995,849 A | 11/1999 | Williams et al. |
| 6,002,363 A | 12/1999 | Krasner |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,023,241 A | 2/2000 | Clapper |
| 6,032,051 A | 2/2000 | Hall et al. |
| 6,034,622 A | 3/2000 | Levine |
| 6,054,928 A | 4/2000 | Lemelson |
| 6,064,336 A | 5/2000 | Krasner |
| 6,067,018 A | 5/2000 | Skelton et al. |
| 6,067,044 A | 5/2000 | Whelan et al. |
| 6,072,396 A | 6/2000 | Gaukel |
| 6,078,290 A | 6/2000 | McBurney et al. |
| 6,083,248 A | 7/2000 | Thompson |
| 6,083,353 A | 7/2000 | Alexander |
| 6,094,168 A | 7/2000 | Duffett-Smith et al. |
| 6,100,806 A | 8/2000 | Gaukel |
| 6,115,595 A | 9/2000 | Rodal et al. |
| 6,131,067 A | 10/2000 | Girerd et al. |
| 6,141,570 A | 10/2000 | O'Neill, Jr. et al. |
| 6,144,303 A | 11/2000 | Federman |
| 6,148,280 A | 11/2000 | Kramer |
| 6,163,696 A | 12/2000 | Bi et al. |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,226,622 B1 | 5/2001 | Dabbiere |
| 6,231,519 B1 | 5/2001 | Blants et al. |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,263,280 B1 | 7/2001 | Stingone, Jr. |
| 6,278,936 B1 | 8/2001 | Jones |
| 6,282,362 B1 | 8/2001 | Murphy et al. |
| 6,292,687 B1 | 9/2001 | Lowell et al. |
| 6,298,306 B1 | 10/2001 | Suarez et al. |
| 6,300,875 B1 | 10/2001 | Schafer |
| 6,302,844 B1 | 10/2001 | Walker et al. |
| 6,314,308 B1 | 11/2001 | Sheynblat et al. |
| 6,317,049 B1 | 11/2001 | Toubia et al. |
| 6,323,807 B1 | 11/2001 | Golding et al. |
| 6,324,213 B1 | 11/2001 | Harrison |
| 6,327,533 B1 | 12/2001 | Chou |
| 6,331,817 B1 | 12/2001 | Goldberg |
| 6,339,397 B1 | 1/2002 | Baker |
| 6,340,928 B1 | 1/2002 | McCurdy |
| 6,342,847 B1 | 1/2002 | Archuleta et al. |
| 6,349,257 B1 | 2/2002 | Liu et al. |
| 6,353,390 B1 | 3/2002 | Beri et al. |
| 6,353,798 B1 | 3/2002 | Green et al. |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,373,430 B1 | 4/2002 | Beason et al. |
| 6,377,810 B1 | 4/2002 | Geiger et al. |
| 6,388,612 B1 | 5/2002 | Neher |
| 6,404,352 B1 | 6/2002 | Ichikawa et al. |
| 6,407,698 B1 | 6/2002 | Ayed |
| 6,411,892 B1 | 6/2002 | Van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,430,602 B1 | 8/2002 | Kay et al. |
| 6,433,732 B1 | 8/2002 | Dutta et al. |
| 6,434,396 B1 | 8/2002 | Rune |
| 6,441,778 B1 | 8/2002 | Durst et al. |
| 6,442,380 B1 | 8/2002 | Mohindra |
| 6,443,890 B1 | 9/2002 | Schulze et al. |
| 6,445,937 B1 | 9/2002 | daSilva |
| 6,453,237 B1 | 9/2002 | Fuchs et al. |
| 6,466,821 B1 | 10/2002 | Pianca et al. |
| 6,469,639 B2 | 10/2002 | Tanenhaus et al. |
| 6,471,087 B1 | 10/2002 | Shusterman |
| 6,478,736 B1 | 11/2002 | Mault |
| 6,505,048 B1 | 1/2003 | Moles et al. |
| 6,513,532 B2 | 2/2003 | Mault et al. |
| 6,522,871 B1 | 2/2003 | Patrick et al. |
| 6,522,889 B1 | 2/2003 | Aarnio |
| 6,529,164 B1 | 3/2003 | Carter |
| 6,544,193 B2 | 4/2003 | Abreu |
| 6,552,652 B2 | 4/2003 | Beken |
| 6,559,620 B2 | 5/2003 | Zhou et al. |
| 6,569,094 B2 | 5/2003 | Suzuki et al. |
| 6,579,231 B1 | 6/2003 | Phipps |
| 6,625,437 B1 | 9/2003 | Jampolsky et al. |
| 6,630,885 B2 | 10/2003 | Hardman et al. |
| 6,640,085 B1 | 10/2003 | Chatzipetros et al. |
| 6,650,907 B1 | 11/2003 | Kamperschroer et al. |
| 6,679,071 B1 | 1/2004 | Storey et al. |
| 6,721,542 B1 | 4/2004 | Anttila et al. |
| 6,747,675 B1 | 6/2004 | Abbott et al. |
| 6,788,766 B2 | 9/2004 | Logan |
| 6,801,853 B2 | 10/2004 | Workman |
| 6,804,606 B2 | 10/2004 | Jones |
| 6,847,892 B2 | 1/2005 | Zhou et al. |
| 6,856,804 B1 | 2/2005 | Ciotta |
| 6,865,385 B1 | 3/2005 | Kohda et al. |
| 6,937,900 B1 | 8/2005 | Pianca et al. |
| 6,952,645 B1 | 10/2005 | Jones |
| 6,975,941 B1 | 12/2005 | Lau et al. |
| 6,980,826 B2 | 12/2005 | Yamaguchi |
| 7,071,842 B1 | 7/2006 | Brady, Jr. |
| 7,085,253 B2 | 8/2006 | Yang |
| 7,136,832 B2 | 11/2006 | Li et al. |
| 7,212,829 B1 | 5/2007 | Lau et al. |
| 7,218,938 B1 | 5/2007 | Lau et al. |
| 7,253,731 B2 | 8/2007 | Joao |
| 7,321,774 B1 | 1/2008 | Lau et al. |
| 7,325,061 B2 | 1/2008 | Haruki |
| 7,366,522 B2 * | 4/2008 | Thomas |
| 7,403,972 B1 * | 7/2008 | Lau et al. ............... 709/206 |
| 2001/0006891 A1 | 7/2001 | Cho |

| | | |
|---|---|---|
| 2001/0020204 A1 | 9/2001 | Runyon et al. |
| 2001/0027378 A1 | 10/2001 | Tennison et al. |
| 2001/0028304 A1 | 10/2001 | I'Anson et al. |
| 2001/0044299 A1 | 11/2001 | Sandegren |
| 2001/0052849 A1 | 12/2001 | Jones, Jr. |
| 2002/0000930 A1 | 1/2002 | Crowson et al. |
| 2002/0016173 A1 | 2/2002 | Hunzinger |
| 2002/0027507 A1 | 3/2002 | Yarin et al. |
| 2002/0038182 A1 | 3/2002 | Wong et al. |
| 2002/0050945 A1 | 5/2002 | Tsukishima et al. |
| 2002/0057192 A1 | 5/2002 | Eagleson et al. |
| 2002/0063622 A1 | 5/2002 | Armstrong et al. |
| 2002/0071677 A1 | 6/2002 | Sumanaweera |
| 2002/0077080 A1 | 6/2002 | Greene |
| 2002/0087260 A1 | 7/2002 | Hancock et al. |
| 2002/0087619 A1 | 7/2002 | Tripathi |
| 2002/0094067 A1 | 7/2002 | August |
| 2002/0111171 A1 | 8/2002 | Boesch et al. |
| 2002/0111819 A1 | 8/2002 | Li et al. |
| 2002/0115453 A1 | 8/2002 | Poulin et al. |
| 2002/0119789 A1 | 8/2002 | Friedman |
| 2002/0120503 A1 | 8/2002 | Iwayama et al. |
| 2002/0193121 A1 | 12/2002 | Nowak et al. |
| 2003/0003943 A1 | 1/2003 | Bajikar |
| 2003/0009410 A1 | 1/2003 | Ramankutty et al. |
| 2003/0013445 A1 | 1/2003 | Fujiwara et al. |
| 2003/0069759 A1 | 4/2003 | Smith |
| 2003/0083011 A1 | 5/2003 | Haller et al. |
| 2003/0151507 A1 | 8/2003 | Andre et al. |
| 2004/0034470 A1 | 2/2004 | Workman |
| 2004/0046637 A1 | 3/2004 | Wesby Van Swaay |
| 2004/0114731 A1 | 6/2004 | Gillett et al. |
| 2004/0117108 A1 | 6/2004 | Nemeth |
| 2004/0233065 A1 | 11/2004 | Freeman |
| 2006/0173444 A1 | 8/2006 | Choy et al. |
| 2008/0021645 A1 | 1/2008 | Lau et al. |
| 2009/0042540 A1 | 2/2009 | Bodnar et al. |

FOREIGN PATENT DOCUMENTS

| | | |
|---|---|---|
| EP | 1 037 447 A2 * | 9/2000 |
| WO | WO 97/41654 * | 11/1997 |
| WO | WO 98/01769 A1 * | 1/1998 |
| WO | WO 98/16045 * | 4/1998 |
| WO | WO 00/51391 * | 8/2000 |
| WO | WO 01/50151 A1 * | 7/2001 |
| WO | WO 02/42979 A1 * | 5/2002 |
| WO | WO 02/084618 A1 * | 10/2002 |
| WO | WO 03/012720 A1 * | 2/2003 |

OTHER PUBLICATIONS

Office Action for U.S. Appl. No. 10/397,474, dated Feb. 27, 2007.
Office Action for U.S. Appl. No. 10/397,474, dated Sep. 6, 2007.
Notice of Allowance for U.S. Appl. No. 10/397,474, dated Mar. 28, 2008.
"352C22 Miniature Low Profile ICP Accelerometer," Precision Accelerometers, PCB Piezoelectronics Products—SVS Division, webpages, pp. 1-2 (downloaded Apr. 11, 2002: www.pcb.com/products/svs/svs352c22.html).*
"3G Mobile Internet Revolution, . . . only with Location Based Services!" pp. 1, (downloaded Aug. 10, 2002: http://webhome.idirect.com/~dental/3glocator/home.htm).*
"Airline Cargo Containers," Case Study, RJI Incorporated, webpages, pp. 1-2 (downloaded Mar. 16, 2002: www.rji.cc/casestudies/airlinecargocontainers.html).*
"Airline Food Carts," Case Study, RJI Incorporated, webpages, pp. 1-2 (downloaded Mar. 16, 2002: www.rji.cc/casestudies/airlinefoodcarts.html).*
"An Introduction to SnapTrack Server-Aided GPS Technology," SnapTrack Inc.
"Audiovox Intros GPS, Bluetooth Phone;" INT Media Group, Inc. (allNetDevices), Apr. 5, 2002. (downloaded: www.allnetdevices.com/wireless/news/2001/1/15/audiovox_intros.html).
"Carrier and end-user applications for wireless location systems," TruePosition, Inc., pp. 1-7.
"Danger -Products" and "Hiphop Communicator Brochure," Danger, Inc., downloaded Oct. 26, 2003: www.danger.com/products.php).

"Developing a GPSs for the Global Supply Chain," Aberdeen Group, Inc., Executive White Paper, Jun. 2002.
"Devices for Text Messages in Deutsche Telekom's fixed network have already found their way into many households," Deutsche Telekom AG, Press Release, Mar. 13, 2002, pp. 1-2.
"Digital/Analog Compass Sensors" and "1655 Digital Compass Sensor," webpages, The Robson Company, Inc., pp. 1-2 (downloaded Apr. 11, 2002: www.dinsmoresensors.com/index.html).
"EarthTrack ™ Vehicle Tracking Systems," Outfitter Satellite, Inc., 1998 (downloaded Jan. 22, 2000).
"Enhanced Tracking," United Parcel Service of America, Inc. (UPS), webpages, pp. 1-2 (downloaded Jun. 1, 2002: www.ups.com/myupsinfo/info/etrack?pnav=stdservice).
"Fleet Management Systems—Asset Tracking Devices," Axiom Navigation Inc., 2000-2001 (downloaded Oct. 19, 2002: www.axiomnav.com/Prod_Systems/prod_system.asp).
"Frozen Food Warehouse," Case Study, RJI Incorporated, webpages, pp. 1-3 (downloaded Mar. 16, 2002: www.rji.cc/casestudies/frozenfoodwarehouse.html).
"FunMail Launches on the NTT DoCoMo i-mode network," FunMail, Press Release, May 1, 2001, pp. 1-2.
"Global Cell Phone Location," Axiom Navigation Inc., 2000-2001 (downloaded Oct. 19, 2002: www.axiomnav.com/Prod_Global/prod_global.asp).
"Global Locating Services," SkyBitz, webpage, p. 1, (downloaded Nov. 15, 2002: www.skybitz.com/services/gls.html).
"GLS Communicator," SkyBitz, webpages, pp. 1-2, (downloaded Nov. 15, 2002: www.skybitz.com/gls/communicator.html).
"Guide to Tracking Info.," Nippon Express, website page, p. 1 (downloaded Jun. 9, 2002: www.nittsu.co.jp/edoc/howtoe.htm).
"Introduction to SMS," by C. Tull of AnywhereYouGo.com, pp. 1-4 (downloaded:www.devx.com/wireless/articles/SMS/SMSintro-asp).
"IO Data Develops GPS Adapter for I-Mode Mobile," AsiaBizTech, Sep. 17, 2002, pp. 1-2.
"Locate Networks: Our Service," Locate Networks, webpages, pp. 1-7 (downloaded Sep. 26, 2002: www.locatenetworks.com/).
"MMS phones: Don't believe the hype," CNN.com/SCI-TECH, Aug. 8, 2002, pp. 1-3.
"Mobile Location Based Services: Cell Tracking Devices of People & Thongs . . . ," pp. 1-2, (downloaded Aug. 10, 2002: http://3glocate.com).
"MoniTrack," Case Study, RJI Incorporated, webpages, pp. 1-2 (downloaded Mar. 16, 2002: www.rji.cc/technology/telematic.html).
"MY UPS.COM Benefits," United Parcel Service of America, Inc. (UPS), webpage, p. 1 (downloaded Apr. 13, 2002: www.ups.com/myupsinfo/info/benefits?pnav=stdsservice).
"NavMate® Navigation System," Visteon Corporation, webpage, pp. 1-2 (downloaded Jun. 21, 2002: www.visteon.com/technology/automotive/navmate.html).
"News," SkyBitz, webpages, pp. 1-8, (downloaded Nov. 15, 2002: www.skybitz.com/about/news.html).
"Pakhound: Your Watchdog in the Shipping Industry," website pages, pp. 1-3 (downloaded Jun. 9, 2002: www.pakhound.com/fact.asp).
"Parkwatch and Wherenet Unveil the First Amusement Visitor Locating system," ParkWatch, Press Release, Jun. 27, 2000.
"pulver.com's Location Based Services Report," pulver.com, Inc., Oct. 2001, pp. 1-17 (downloaded Jun. 4, 2002: www.pulver.com/lbsreport/lastbsreport.02/oct01.txt).
"Radio Frequency Identification (RFID)," Case Study, RJI Incorporated, webpage, p. 1 (downloaded Mar. 16, 2002: www.rji.cc/technology/rfid.html).
"Real Time Location System (RTLS)," Case Study, RJI Incorporated, webpage, p. 1 (downloaded Mar. 16, 2002: www.rji.cc/technology/rtls.html).
"Real-Time Warehouse Tracking," Case Study, RJI Incorporated, webpages, pp. 1-2 (downloaded Mar. 16, 2002: www.rji.cc/casestudies/rtwarehousetracking.html).
"Savi Reusable Transport Container," Savi Technology, Inc., Apr. 30, 2002, pp. 1-2.
"Send images to i-mode phones," Mobile Media Japan, 2001, pp. 1-3.

"Ski Rental with Auto ID and Tracking," Case Study, RJI Incorporated, webpages, pp. 1-2 (downloaded Mar. 16, 2002: www.rji.cc/casestudies/skirentalcompany.html).

"SnapTrack and SignalSoft Corp. Team Up to Trial Location-based Information Service for GSM Test Group," Press Release, SnapTrack Inc., Dec. 6, 1999.

"SnapTrack Awarded Additional Key Patents for Enhanced GPS System," Press Release, SnapTrack Inc., Jan. 4, 2000.

"Start-up crams single chip with phone, GPS and Bluetooth," CNET Network, Inc. (ZDNET), Mar. 22, 2002 (downloaded: http://news.zdnet.co.uk/story/0,t284-x2107163,00.html).

"Status Icons/Messages," Yahoo! Messenger Help, Yahoo! Inc., 2002, pp. 1-2.

"Technical Applications of Our Current Technology," Aetherwire, webpages, pp. 1-4 (downloaded Mar. 16, 2002: www.aetherwire.com/CDROM/General/appl1.html).

"The Always on Network," Position Paper, Nortel Networks, 2002.

"Theme Park Visitors & Cashless Purchasing," Case Study, RJI Incorporated, webpages, pp. 1-2 (downloaded Mar. 16, 2002: www.rji.cc/casestudies/themepark.html).

"Track Shipments—Detailed Results," FedEx, webpages, pp. 1-2 (downloaded Oct. 29, 2002: www.fedex.com).

"Track Your FedEx Shipments via Email," FedEx, webpages, pp. 1-2 (downloaded Oct. 29, 2002: www.fedex.com).

"Tracking Helpful Tips," United Parcel Service of America, Inc. (UPS), webpages, pp. 1-2 (downloaded Jun. 1, 2002: www.ups.com/tracking/nm_help.html).

"Trimble and Rosum Team to Develop Universal Positioning Technology," Trimble Navigation, Inc., News Release, Feb. 27, 2003.

"Turning Position Into Knowledge," SkyBitz, webpage, p. 1, (downloaded Nov. 15, 2002: www.skybitz.com).

"UPS Package Tracking," United Parcel Service of America, Inc. (UPS), webpages, pp. 1-2 (downloaded Apr. 13, 2002: www.ups.com/tracking/tracking.html).

"UPS Wireless Solutions," United Parcel Service of America, Inc. (UPS), webpage, p. 1 (downloaded Apr. 13, 2002: www.ups.com/myupsinfo/info/wireless?pnav=stdsservice).

"Welcome to Iship, Inc.," iShip, Inc., webpages, pp. 1-2, (downloaded Jun. 9, 2002: www.iship.com/).

"Welcome to Traker Systems," Tracker Systems, webpages, pp. 1-2 (downloaded Jun. 9, 2002: www.trakersystems.com).

"What are Instant Messages?" Yahoo! Messenger Help, Yahoo! Inc., 2002, pp. 1.

"What is "3G" technology?," CNN.com/SCI-TECH, Oct. 22, 2001, pp. 1-3.

"What is a Friend List?" Yahoo! Messenger Help, Yahoo! Inc., 2002, pp. 1.

"Wherify Wireless and SiRF Team to Deliver Child Locator System," Wherify Wireless, Inc., Press Release, Mar. 19, 2001, pp. 1-2.

"Wherify Wireless Breakthrough in Location-Based Services," Mobilemag.com, Feb. 28, 2001, p. 1.

"Wherify Wireless GPS Locator for Kids User Guide," Wherify Wireless, Inc., 2003, pp. 1-106.

"Wherify Wireless Location Services," Wherify Wireless, Inc., webpages, pp. 1-5 (downloaded: Mar. 25, 2003: www.wherifywireless.com/prod_watches.htm).

"X-GPS™—Hybrid GPS Location Server Solution," Axiom Navigation Inc., 2000-2001 (downloaded Oct. 19, 2002: www.axiomnav.com/Prod_Global/x-gps.asp).

"Yahoo! Messenger—Sending Messages to a Mobile Phone," Yahoo! Messenger, Yahoo! Inc., 2002, pp. 1-7 (downloaded Oct. 27, 2002: http://messenger.yahoo.com/messenger/wireless/pc2sms/tour1.html(through/tour7.html)).

"Yahoo! Messenger for Text Messaging," Yahoo! Messenger, Yahoo! Inc., 2002, pp. 1-10 (downloaded Oct. 27, 2002: http://messenger.yahoo.com/messenger/wireless/smsmsgr/tour1.html (through/tour7.html)).

"Yahoo! Messenger for WAP," Yahoo Messenger, Yahoo! Inc., 2002 (tours 1-9), pp. 1-17 (downloaded Oct. 27, 2002: www.messenger.yahoo.com/messenger/wireless/wap/tour1.html(through/tour9.html)).

Accelerometers—General Purpose, LP Series, Crossbow Technology, Inc., data sheet, pp. 1-3 (downloaded Apr. 11, 2002: www.xbow.com/Products/Accelerometers.htm).

Bickers, "Eyes in the sky," SafeTzone Technology Corporation, webpages, 2001, pp. 1-3 (downloaded: www.safetzone.com/newsKiosk.asp).

Chertkoff, Rachel, "Vehicle Locator Systems," Pager Technology, pp. 1-2, 1998.

Commercial Uses for LoJack (webpage), LoJack Corporation, downloaded Jan. 22, 2000.

Crossbow Product Guide—Accelerometers, Crossbow Technology, Inc., webpages, pp. 1-3 (downloaded Apr. 11, 2002: www.xbow.com/Products/Accelerometers.htm).

Delphi and MobileAria Demonstrate True Hands Free In-Vehicle Mobile Productivity Services At CES, Press Release, Delphi Automotive Systems, Jan. 8, 2002 (downloaded Apr. 5, 2002: www.delphiauto.com/news/pressRelease/pr6828-01082002).

F. Rivera, "Special Report: Keeping Tabs on Your Teen," 7 News, Boston, Apr. 30, 2002, pp. 1-3.

FedEx Insight, FedEx, webpages, pp. 1-11 (downloaded Oct. 29, 2002: www.fedex.com).

GPS2000, Omega Research and Development, Inc., webpages, pp. 1-9 (pp. 7-9 pertain to an online tour) (downloaded Jul. 14, 2003: www.gps2000online.com/).

IMVironment, Yahoo! Messenger Yahoo! Inc., 2002, pp. 1-12 (downloaded (including) Oct. 27, 2002: http://help.yahoo.com/help/us/mesg/imv/imv-01.html(through /index5.html).

J.Wrolstad, "Chrysler Claims First With Bluetooth Mobile Phone System," Wireless Newsfactor, Oct. 26, 2001.

K. Hill, "Prada Uses Smart Tags to Personalize Shopping," CRMDaily.com, Apr. 24, 2002., pp. 1-4.

K. Miyake, "Sharp to unveil 3G PDA-type cell phone," ITworld.com, Inc., Jan. 11, 2002.

Kleinknecht, William, "Juvenile authorities want satellite tracking for felons," The Star-Ledger of New Jersey, Nov. 18, 1997.

LoadTrak, pp. 1-2 (downloaded Jun. 4, 2002: www.load-trak.com).

Marek, "The Unstoppable SnapTrack," Wireless Week, Dec. 18, 2000.

Motorola Consumer Catalog: Pagers (webpage), Motorola, Inc., downloaded Jan. 19, 2000.

My.Roadway!, Roadway Express, Inc., webpages, pp. 1-2, (downloaded Jun. 9, 2002: www.quiktrak.roadway.com/cgi-bin/quiktrak).

Packtrack™, PackTrack.com, webpages, pp. 1-2 (downloaded Jun. 9, 2002: www.packtrack.com).

Precision Accelerometers, PCB Piezoelectronics Products—SVS Division, webpages, pp. 1-2 (downloaded Apr. 11, 2002: www.pcb.com/products/svs/index.html).

Rabinowitz and Spilker, Jr., "A New Positioning System Using Television Synchronization Signals," Rosum Corporation, pp. 1-11 (downloaded May 21, 2003).

Rabinowitz and Spilker, Jr., "Positioning Using the ATSC Digital Television Signal," Rosum Corporation Whitepaper, Rosum Corporation (downloaded May 21, 2003).

Real Time Locating System, Executive Summary, Technology Systems International, Inc., 2007.

Ryan, "Catching up with Dick Tracy," San Francisco Chronicle, news article, Mar. 18, 2002.

SandPiper GPS Receiver, Specification sheet by Axiom Navigation Inc. (www.axiomnav.com), 2006.

Smart Antenna, Specification sheet by Axiom Navigation Inc. (www.axiomnav.com), 2008.

SnapTrack—Privacy Protection (webpage), SnapTrack Inc., downloaded Jan. 19, 2000.

SnapTrack—Technology At Work (webpage), SnapTrack Inc., downloaded Jan. 19, 2000.

SnapTrack in Action (webpage), SnapTrack Inc., downloaded Jan. 19, 2000.

Stilp, Louis A., "Examining the Coming Revolution in Location Services," pp. 1-11, 1997.

Swift A2 GPS Receiver, Specification sheet by Axiom Navigation Inc. (www.axiomnav.com), 2010.

TruePosition Virtual Brochure (webpage), TruePosition, Inc.

Wong, "Fishers, golfers join the rush to GPS," San Jose Mercury News, news article, Mar. 25, 2002.

* cited by examiner

METHOD AND SYSTEM FOR ENHANCED MESSAGING

CROSS REFERENCE TO RELATED APPLICATIONS

This application is a continuation of U.S. patent application Ser. No. 10/397,474, filed Mar. 26, 2003, now U.S. Pat. No. 7,403,972, and entitled "METHOD AND SYSTEM FOR ENHANCED MESSAGING" which is hereby incorporated herein by reference, and which in turn claims benefit of: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

This application is also related to: (i) U.S. patent application Ser. No. 10/397,473, filed Mar. 26, 2003, now U.S. Pat. No. 6,975,941, and entitled "METHOD AND APPARATUS FOR INTELLIGENT ACQUISITION OF POSITION INFORMATION;" (ii) U.S. patent application Ser. No. 10/397,472, filed Mar. 26, 2003, now U.S. Pat. No. 7,218,938, and entitled "METHODS AND APPARATUS TO ANALYZE AND PRESENT LOCATION INFORMATION;" (iii) U.S. patent application Ser. No. 10/397,637, filed Mar. 26, 2003, now U.S. Pat. No. 7,212,829, and entitled "METHOD AND SYSTEM FOR PROVIDING SHIPMENT TRACKING AND NOTIFICATIONS;" (iv) U.S. patent application Ser. No. 10/397,641, filed Mar. 26, 2003, and entitled "METHOD AND SYSTEM FOR PERSONALIZED MEDICAL MONITORING AND NOTIFICATIONS THEREFOR;" (v) U.S. patent application Ser. No. 10/397,640, filed Mar. 26, 2003, now U.S. Pat. No. 7,321,774, and entitled "INEXPENSIVE POSITION SENSING DEVICE;" (vi) U.S. patent application Ser. No. 10/397,512, filed Mar. 26, 2003, and entitled "APPLICATIONS OF STATUS INFORMATION FOR INVENTORY MANAGEMENT."

BACKGROUND OF THE INVENTION

1. Field of the Invention

The present invention relates to communication devices and, more particularly, to enhanced messaging for communication devices.

2. Description of the Related Art

Today, electronic mail (email) is a common mode of communication. One person, acting as a sender, composes an email message and then sends the email message to another person designated as a recipient. The sender composes the email message by interacting with a communication device. The recipient is able to read the email message by interacting with another communication device. Communication devices are often personal computers or mobile telephones. These communication devices can receive and transmit electronic mail messages over a network. The network can be public or private as well as wired or wireless.

Although email is an effective means of communication, when a sender is using a mobile telephone, composing an email message can be tedious and difficult. User interfaces can provide limited assistance to users such as by creating email messages through word prediction, predetermined responses, etc. Nevertheless, given the difficulties with composing messages, email messages from mobile telephones in most cases are relatively short. Recently, communication devices, including mobile telephones, have been able to send and receive instant messages, which are short text messages sent and received in near real time between communication device.

Apart from sending and receiving email messages, mobile telephones can also display the location or availability (i.e., online or offline) of other users via their mobile telephones. This information is provided by a wireless service provider that monitors location or availability of users via their mobile phones. Unfortunately, such information needs the assistance of wireless service providers and tends not to be widely available. Moreover, if such information is available, the information would very likely not be current and thus the usefulness of the information would be limited.

Thus, there is a need for improved approaches to enhance the capabilities of messaging.

SUMMARY OF THE INVENTION

Broadly speaking, the invention relates to techniques for acquiring, sending, receiving or using status information from a remote location over a network. The status information is transmitted by electronic devices over the network. The status information can be provided by one or more sensors associated with the electronic device that is transmitting the status information. The status information can be transmitted with messages so as to enhance the messages.

According to one aspect of the invention, base messages are entered by a user or automatically produced. The base messages can be text messages (including instant messages), voice messages, video messages or other types of messages. The base messages are augmented to additionally include status information, such as position and/or other conditions information. The status information is normally provided by one or more sensors. In one implementation, base messages can be combined with status information, whereby the resulting messages are referred to as enhanced messages. These enhanced messages are electronically sent from and received at electronic devices, such as personal computers and mobile communication devices.

The invention can be implemented in numerous ways including, a method, system, device, graphical user interface, and a computer readable medium. Several embodiments of the invention are discussed below.

As a method implemented by a computing device for communicating between users of mobile communication devices, one embodiment of the invention can, for example, include at least: obtaining a message at a first mobile communication device to be delivered to a second mobile communication device; acquiring status information at the first mobile communication device, the status information including at least position information associated with the first mobile communication device; associating the status information to the message; and sending the message along with the status information from the first mobile communication device to the second mobile communication device. In one embodiment, the message is from a user of the first mobile communication device, and the message is to be delivered to another user via the second mobile communication device. The message can contain content chosen by the user of the first mobile communication device and the message is distinct from the status information.

As a method implemented by a computing device for communicating between users of mobile communication devices, another embodiment of the invention can, for example, include at least: obtaining a message at a first mobile communication device to be delivered to a second mobile communication device; acquiring status information at the first mobile communication device, the status information including at least position information associated with the first mobile communication device; and determining whether the second mobile communication device or a user thereof is authorized to obtain the status information of the first mobile communication device. If it is determined that the second mobile communication device or a user thereof is authorized to obtain the status information of the first mobile communication device, the method can further include at least (i) associating the status information to the message, and (ii) sending the message along with the status information from the first mobile communication device to the second mobile communication device. In one embodiment, the message is from a user of the first mobile communication device, and the message is to be delivered to another user via the second mobile communication device. The message can contain text chosen by the user of the first mobile communication device and the message is distinct from the status information.

As a method for displaying a message on a display for a user of a wireless communication device, one embodiment of the invention can, for example, include at least: receiving a message from another wireless communication device over a network; determining whether the message includes at least status information; extracting the status information from the message when said determining determines that the message includes at least the status information; and displaying the message and at least one representation of the status information on the display following said extracting when said determining determines that the message includes at least the status information. In one embodiment, the message is initiated by a user of the another wireless communication device, the message can contain text chosen by the user of the another computing device, and the message is different from the status information.

As a method implemented by a computing device for communicating between users of mobile communication devices, another embodiment of the invention can, for example, include at least: obtaining a message at a first mobile communication device to be delivered to a plurality of other mobile communication devices; acquiring status information at the first mobile communication device, the status information including at least position information associated with the first mobile communication device; and determining whether the plurality of other mobile communication devices or users thereof are authorized to obtain the status information of the first mobile communication device. If it is determined that the plurality of other mobile communication devices or users thereof are authorized to obtain the status information of the first mobile communication device, the method can further include at least broadcasting the message along with the status information from the first mobile communication device to each of the plurality of other mobile communication devices. In one embodiment, the message is from a user of the first mobile communication device, the message can contain content chosen by the user of the first mobile communication device, and the message is distinct from the status information.

As a computer readable medium including at least executable computer program code tangibly stored therein for communicating between users of mobile communication devices, one embodiment of the invention can, for example, include at least: computer program code for receiving a message at a first mobile communication device to be delivered to a second mobile communication device; computer program code for acquiring status information at the first mobile communication device, the status information including at least position information associated with the first mobile communication device; computer program code for determining whether the second mobile communication device or a user thereof is authorized to obtain the status information of the first mobile communication device; computer program code for associating the status information to the message if it is determined that that the second mobile communication device or a user thereof is authorized to obtain the status information of the first mobile communication device; and computer program code for sending the message along with the status information from the first mobile communication device to the second mobile communication device if it is determined that that the second mobile communication device or a user thereof is authorized to obtain the status information of the first mobile communication device. In one embodiment, the message is from a user of the first mobile communication device, and the message is to be delivered to another user via the second mobile communication device. The message can contain text chosen by the user of the first mobile communication device and the message is distinct from the status information.

As a computer readable medium including at least executable computer program code tangibly stored therein for displaying a message on a display for a user of a wireless communication one device, embodiment of the invention can, for example, include at least: computer program code for receiving a message from another wireless communication device over a network; computer program code for determining whether the message includes at least status information; computer program code for extracting the status information from the message when said determining determines that the message includes at least the status information; and computer program code for displaying the message and at least one representation of the status information on the display when said computer program code for determining determines that the message includes at least the status information. In one embodiment, the message is initiated by a user of the another wireless communication device, the message can contain content chosen by the user of the another computing device, and the message is different from the status information.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

The invention relates to techniques for acquiring, sending, receiving or using status information from a remote location over a network. The status information is transmitted over the network between or among electronic devices. The status information can be provided by one or more sensors associated with the electronic device that is transmitting the status information. The status information can be transmitted with messages so as to enhance the messages. The electronic devices include at least computing devices, such as personal computers, personal digital assistants, pagers, and mobile telephones.

According to one aspect of the invention, messages are enhanced through use of status information. Base messages are entered by a user or automatically produced. The base messages can be text messages (including instant messages), voice messages, video messages or other types of messages. The base messages are augmented to additionally include status information, such as position and/or other conditions information. The status information is normally provided by one or more status sensors. In one implementation, base messages can be combined with status information, whereby the resulting messages are referred to as enhanced messages. These enhanced messages are electronically sent from and received at communication devices, such as personal computers and mobile communication devices.

Different embodiments of the invention are discussed below with reference to FIGS. 1-7. However, those skilled in the art will readily appreciate that the detailed description given herein with respect to these figures is for explanatory purposes as the invention extends beyond these limited embodiments.

According to one aspect of the invention, traditional messages transmitted between communication devices are augmented to additionally include status information, such as position and/or conditions information. The conditions information can pertain to one or more of environmental conditions, device-related conditions, or user-related conditions. One or more status sensors associated with the communication devices can capture or obtain the status information. In the case of position information, the status sensor can be a receiver, such as a Global Positioning System (GPS) receiver or other means.

Figure 1:
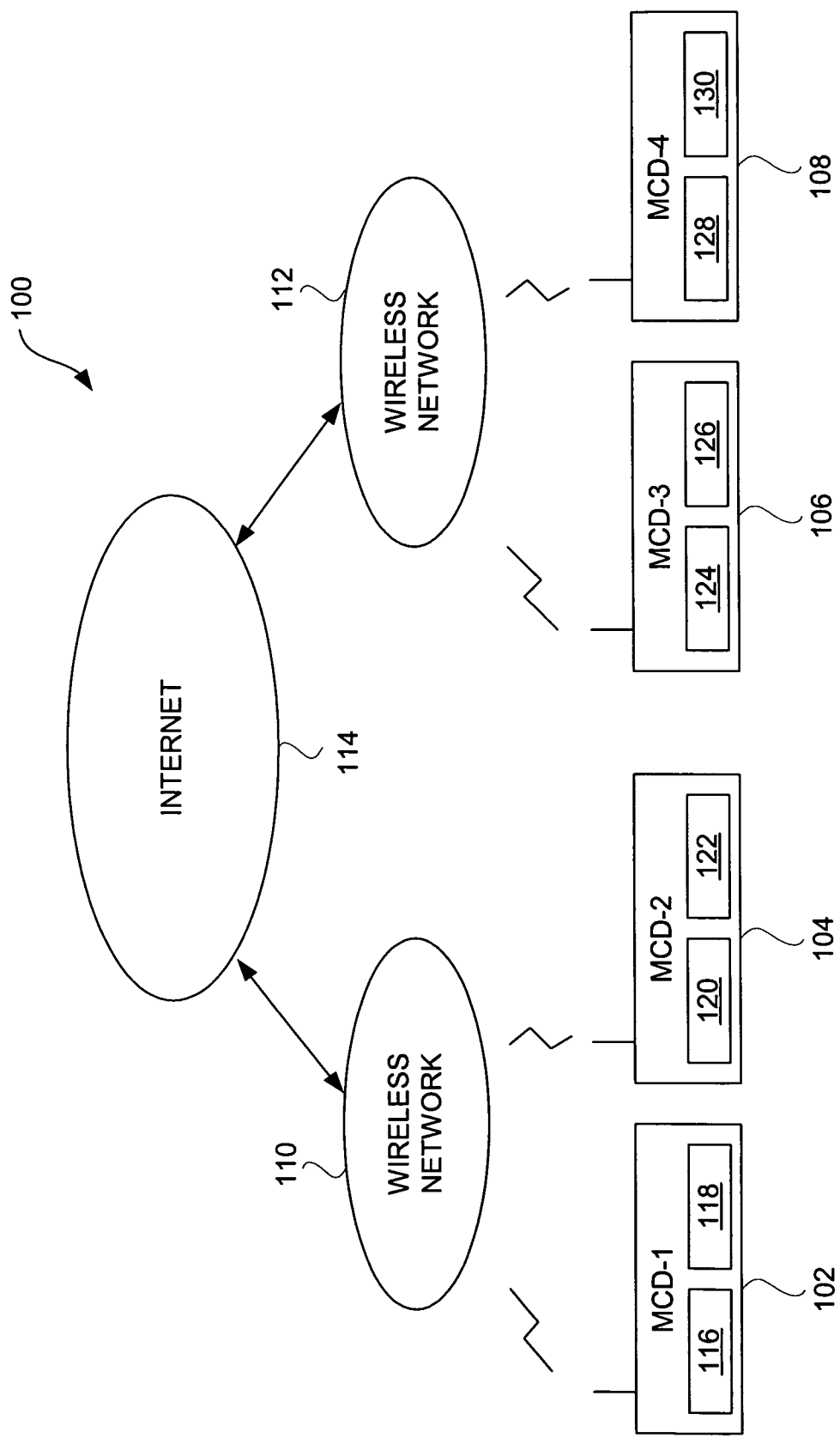
FIG. 1 is a block diagram of an enhanced messaging system according to one embodiment of the invention.

FIG. 1 is a block diagram of an enhanced messaging system 100 according to one embodiment of the invention. The enhanced messaging system 100 allows electronic messages (e.g., text messages) to be sent between mobile communication devices. The electronic messages being sent can be enhanced to include status information pertaining to (i) status of the associated mobile communication devices, (ii) status associated with the environment of the mobile communication devices, and/or (iii) status of the person(s) using the mobile communication device(s).

The enhanced messaging system 100 includes mobile communication devices 102, 104, 106 and 108. The mobile communication devices 102 and 104 communicate with a wireless network 110, and the mobile communication devices 106 and 108 communicate with a wireless network 112. The wireless networks 110 and 112 can be the same or different networks and can utilize same or different protocols. The wireless networks 110 and 112 can be coupled together and/or can couple to the Internet 114, and can support global messaging.

The enhanced messages are sent from one of the mobile communication devices to one or more other of the mobile communication devices. These enhanced messages can include additional information about the mobile communication device, its user and/or its environment. In one embodiment, the status information can include at least position (location) information and other status information. To provide the status information, the mobile communication devices 102, 104, 106 and 108 can include one or more status sensors, such as position detectors, and/or one or more other types of condition sensors for different conditions regarding the communication devices. A position detector can provide position information pertaining to its corresponding mobile communication device. Similarly, a condition sensor provides condition information pertaining to conditions sensed at the corresponding mobile communication device. More particularly, the mobile communication device 102 includes a position detector 116 and at least one condition sensor 118; the mobile communication device 104 includes a position detector 120 and at least one condition sensor 122; the mobile communication device 106 includes a position detector 124 and at least one condition sensor 126; and the mobile communication device 108 includes a position detector 128 and at least one condition sensor 130.

In one embodiment, the position information is obtained from a global positioning system (GPS) receiver, which can be in a mobile communication device. In other words, the position detector can be a GPS receiver. The position information can be obtained or augmented by a local positioning system such as utilized with a local network (e.g., Bluetooth, Wi-Fi, etc.). The conditions information can vary with application. Examples of conditions that can be provided within the conditions information include environment conditions or conditions of the environment of the corresponding mobile communication device. Environment conditions include temperature, humidity, pressure, gaseous or liquid states, chemical compositions, wind speed, color composition, scent, light, sound, smoke, particle or radiation (e.g., infrared radiation). The conditions information can be pertaining to a mobile communication device itself, such as force or pressure asserted on it, or its vibration, acceleration, speed (velocity) or direction. The conditions information can also include user-related conditions. These are conditions related to the user, who is typically a living being and who may be using the corresponding mobile communication device. Examples of user-related conditions include the being's physical conditions (e.g., heart beat, temperature, pupil dilation, hunger, perspiration, tired or sick), volitional behavior (e.g., facial expressions, jumping or moving), or the user's emotional state, such as the user's mood. Examples of emotional states or moods include sad, happy, mad, stressed, or excited. Some of these conditions are not determined directly by sensors, but are instead determined indirectly through processing other sensor data.

In one embodiment, an enhanced messaging system can operate in a distributed manner with little or no centralized management for status information exchange. In other words, the exchange of status information can be peer-to-peer (e.g., from one mobile communication device to another) without an intermediate centralized server to store and manage distribution of the status information. Such an embodiment can operate without assistance from wireless networks service providers. The enhanced messaging system 100 shown in FIG. 1 is suitable for use as such an embodiment.

In another embodiment, an enhanced messaging system can operate in a centralized manner, such as shown below in FIG. 2. In the case of a centralized system, or at least one providing centralized assistance, the status information can be stored and/or processed by a separate entity, independent of the parties sending and receiving information.

Figure 2:
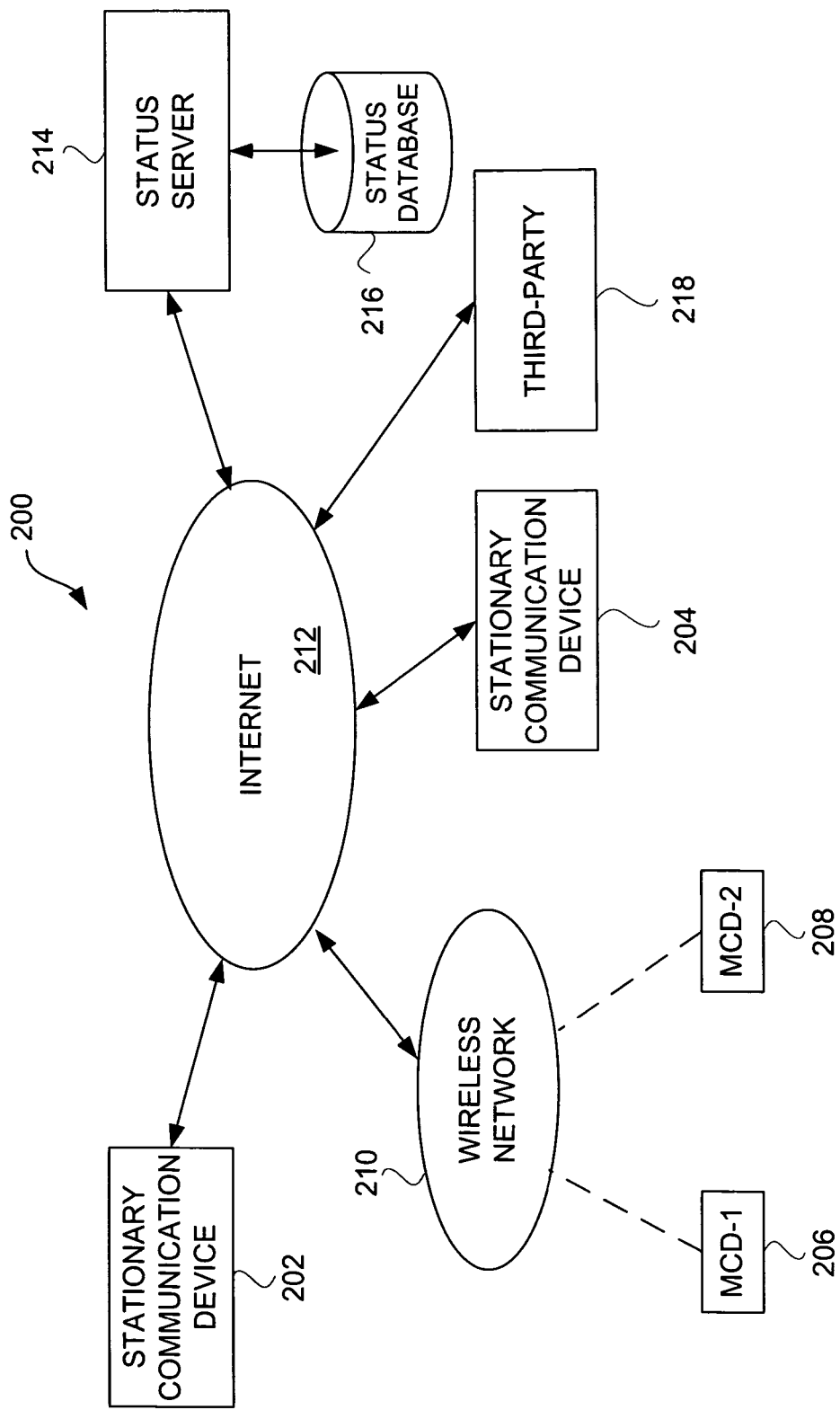
FIG. 2 is a block diagram of an enhanced messaging system according to another embodiment of the invention.

FIG. 2 is a block diagram of an enhanced messaging system 200 according to one embodiment of the invention. The enhanced messaging system 200 provides web-based enhanced messaging between users of communication devices. The enhanced messages being sent from one of the communication devices to one or more other of the communication devices. These enhanced messages can include additional information pertaining to a communication device, its user and/or its environment. In one embodiment, the status information can include at least position (location) information and conditions information.

According to the embodiment shown in FIG. 2, the enhanced messaging system 200 includes stationary communication devices 202 and 204. The enhanced messaging system 200 also includes mobile communication devices (MCD) 206 and 208. Typically, the mobile communication devices 206 and 208 are worn by, affixed to or carried by users. The enhanced messaging system 200 would normally be able to support multiple stationary communication devices, such as desktop computers, and mobile communication devices, such as mobile telephones, personal digital assistants and two-way pagers.

In general, messages can be transmitted (sent and/or received) between and/or among any of the communication devices, regardless of whether stationary or mobile. For discussion, it is assumed that a message is created and sent from the mobile communication device 206 to the stationary communication device 204. The message is assumed to be a text message, such as a real-time text message (e.g., instant message). In this example, the mobile communication device 206 acquires status information pertaining to the user, the device and/or the environment. The acquired status information is provided to the stationary communication device 204 along with the message.

The mobile communication devices 206 and 208 couple to a wireless network 210. The wireless network 210 couples to the Internet 212. Further, a status server 214 is coupled to the Internet 212. The status server 214 also couples to a status database 216. The Internet 212 can be replaced by other data networks (e.g., enterprise network, regional network, Local Area Network, Wide Area Network and global network).

The status information can include at least position (location) information and conditions information. The position information is obtained typically from a global positioning system (GPS) receiver within the first mobile communication device 206. The position information can be obtained or augmented by a local positioning system such as utilized with a local network (e.g., Bluetooth, Wi-Fi, etc.).

The conditions information can vary with application. Various examples of conditions that can be provided within the conditions information were noted above. The corresponding conditions sensor(s) can also be in the mobile communication device 206, or the sensor(s) can be wired or wirelessly coupled to the mobile communication device 206.

The status information that is obtained by the first mobile communication device 206 is sent by the first mobile communication device 206 to the status server 214 via the wireless network 210 and the Internet 212. The status server 214 stores the status information pertaining to the first mobile communication device 206 into the status database 216 such that it is associated with the first mobile communication device 206. The status server 214 monitors status information for numerous communication devices, including mobile communications devices and/or stationary communication device, and thus stores status information pertaining to numerous communication devices.

The enhanced messaging system 200 can also include at least one third-party 218. The third-party 218 is a user interested in status information acquired by mobile communication devices but does not normally receive the text messages also being sent.

The enhanced messaging system 200 can allow a recipient of the message to not only receive the text of the message but also the status information associated with the message. In one embodiment, the recipient receives the status information with the message. The recipient of the message can, for example, include one or more of the mobile communication devices 206 and 208 or one or more of the stationary communication devices 202 and 204, or users thereof. In another embodiment, an authorized party, such as the user of the stationary communication devices 202 and 204 or the third-party 218, can interact with the status server 214 through a web interface so that such users are able to access certain status information via the status server 214 and the status database 216. The web interface can facilitate a user in accessing status information anytime anywhere.

Figure 3:
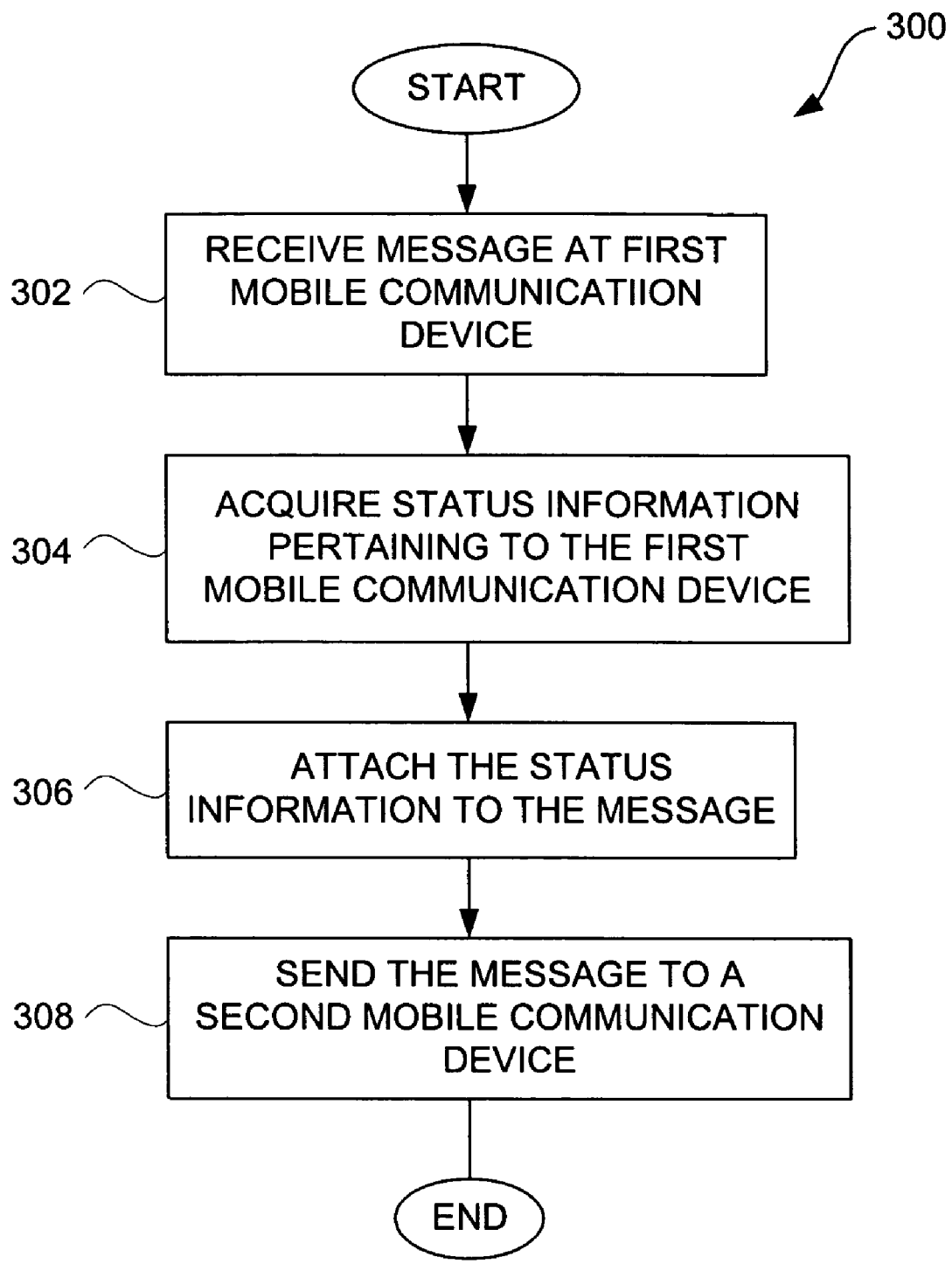
FIG. 3 is a flow diagram of status message processing according to one embodiment of the invention.

FIG. 3 is a flow diagram of status message processing 300 according to one embodiment of the invention. The status message processing 300 is, for example, performed by a mobile communication device (e.g., mobile telephone, two-way pager) or other computing device (e.g., desktop computer, gateway, server).

Initially, the status message processing 300 receives 302 a message at a first mobile communication device. For example, a user of the mobile communication device would typically interact with the mobile communication device (e.g., through a user interface) to create the message. Hence, in this embodiment, the message is considered to be a user-entered message. The user-entered message can be a voice message, a text message, a video message or some other type of input, or some combination thereof. A text message is, for example, a standard email message, a short message (e.g., SMS message) or an instant message. Status information pertaining to the first mobile communication device (and/or its user or environment) can be acquired 304. As noted above, in one embodiment, the status information can include at least position (location) information and/or conditions information. Some or all of the status information can then be attached 306 to the user-entered message. In one embodiment, at least some of the status information has been processed before attachment. The processed status information is still considered as status information. With the status information attached 306 to the user-entered message, the user-entered message becomes an enhanced message. The enhanced message is then sent 308 from the first mobile communication device to another electronic device, such as a second mobile communication device (e.g., mobile telephone, personal digital assistant, or pager) or other computing device (e.g., portable or stationary computer). Typically, the sending of the enhanced message involves electronic transmission of the enhanced message over a wireless network as well as perhaps a wired network. Although the enhanced message is often sent from one mobile communication device to another mobile communication device, the message can alternatively be sent to another computing device, such as a personal computer coupled to the network. Following the operation 308, the status message processing 300 is complete and ends.

Figure 4:
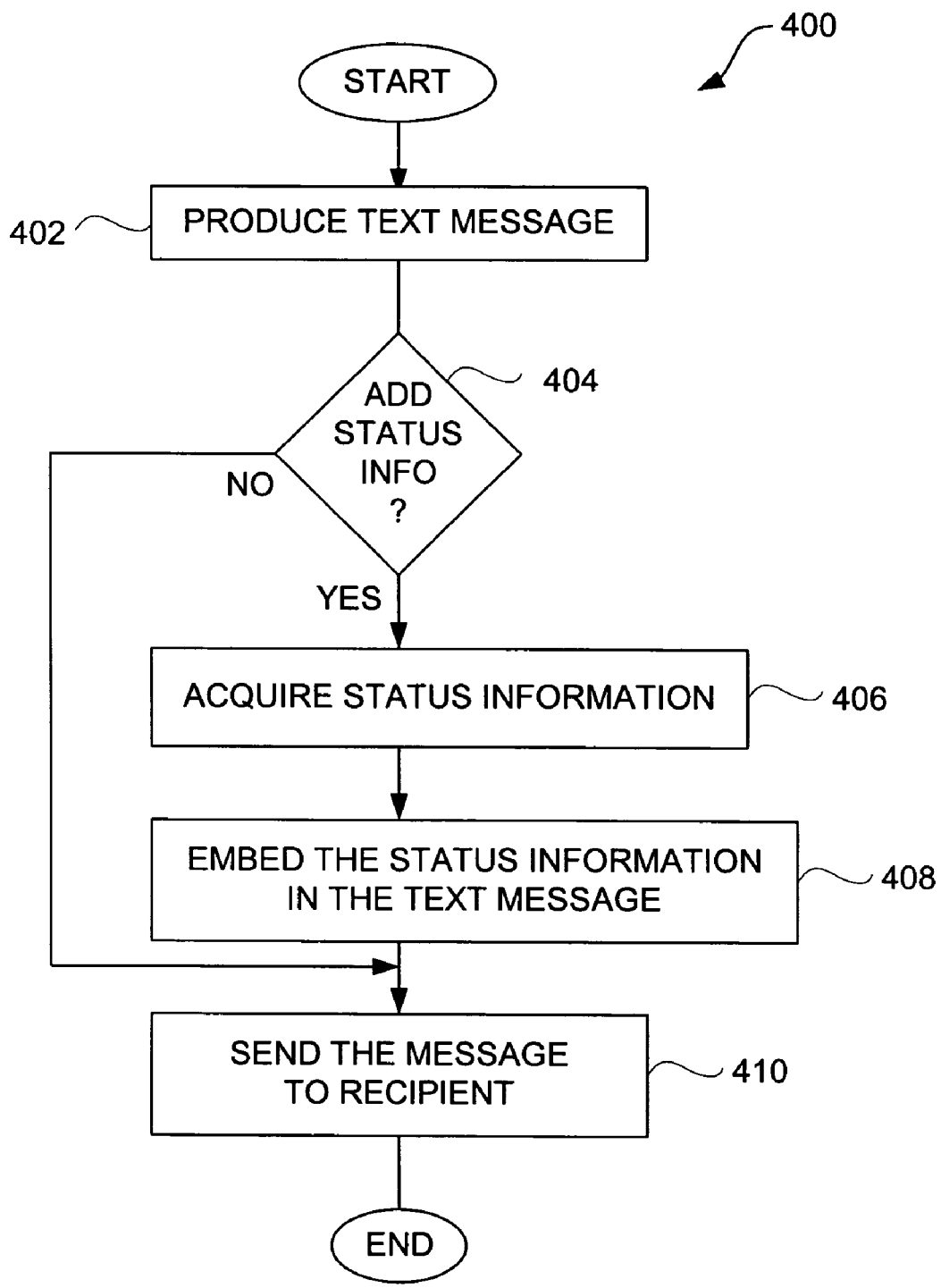
FIG. 4 is a flow diagram of send processing according to one embodiment of the invention.

FIG. 4 is a flow diagram of send processing 400 according to one embodiment of the invention. The send processing 400 is, for example, performed by a mobile communication device or other computing device.

The send processing 400 initially produces 402 a message. In this embodiment, the message is a user-entered message such as a text message. The text message can, for example, be produced or initiated by a user of the mobile communication device or other computing device. However, in other embodiment, the message can be a voice message or a video message.

A decision 404 then determines whether status information is to be added to the text message. The decision 404 allows the user to limit or restrict the status information that is sent to others. For example, the user might restrict the status information such that it can only be sent to authorized persons or destinations. The restrictions can be imposed by a profile or configuration information associated with the user. In one implementation, a user can make use of a list of recipients permitted to receive status information (e.g., pre-authorized recipients). As another example, a dialog box (or other graphical user interface) could be displayed to allow the user to select none, some or all of the available status information to be sent generally with all text messages, or specifically with a particular text message. As still another example, default authorizations can control the status information that is to be sent to recipients. Yet, in another example, status information can have different levels. Some levels can be more confidential than others, or some levels can be more important than others. These levels can also be set by the user. Regardless, different recipients can receive different levels of status information.

In any case, when the decision 404 determines that status information is to be provided with the text message, the status information is acquired 406. The status information is acquired from the mobile communication device or other computing device that is sending the text message. For example, the status information can be acquired 406 from a position detector and at least one condition sensor within (wired or wirelessly coupled to) the mobile communication device.

Regardless of how or when acquired, the status information can then be embedded 408 in the text message. Once the status information has been embedded in 408 (or otherwise combined with or linked to) the text message, the resulting message is referred to as an enhanced message. The status information can be embedded in an open (e.g., as additional displayed information) or hidden manner (e.g., as undisplayed text). In one example, the status information is embedded in the text message using a markup language. The status information being embedded in the text message can also be encrypted, or the entire enhanced message can be encrypted. After the status information is embedded 408 (as well as directly after the decision 404 when no status information is to be added, the resulting message (regardless of whether enhanced or not) is sent 410 to a recipient. The recipient is typically a user of another mobile communication device or other computing device. However, the recipient can also be the another mobile communication device or other computing device. Following the operation 410, the send processing 400 is complete and ends.

Figure 5:
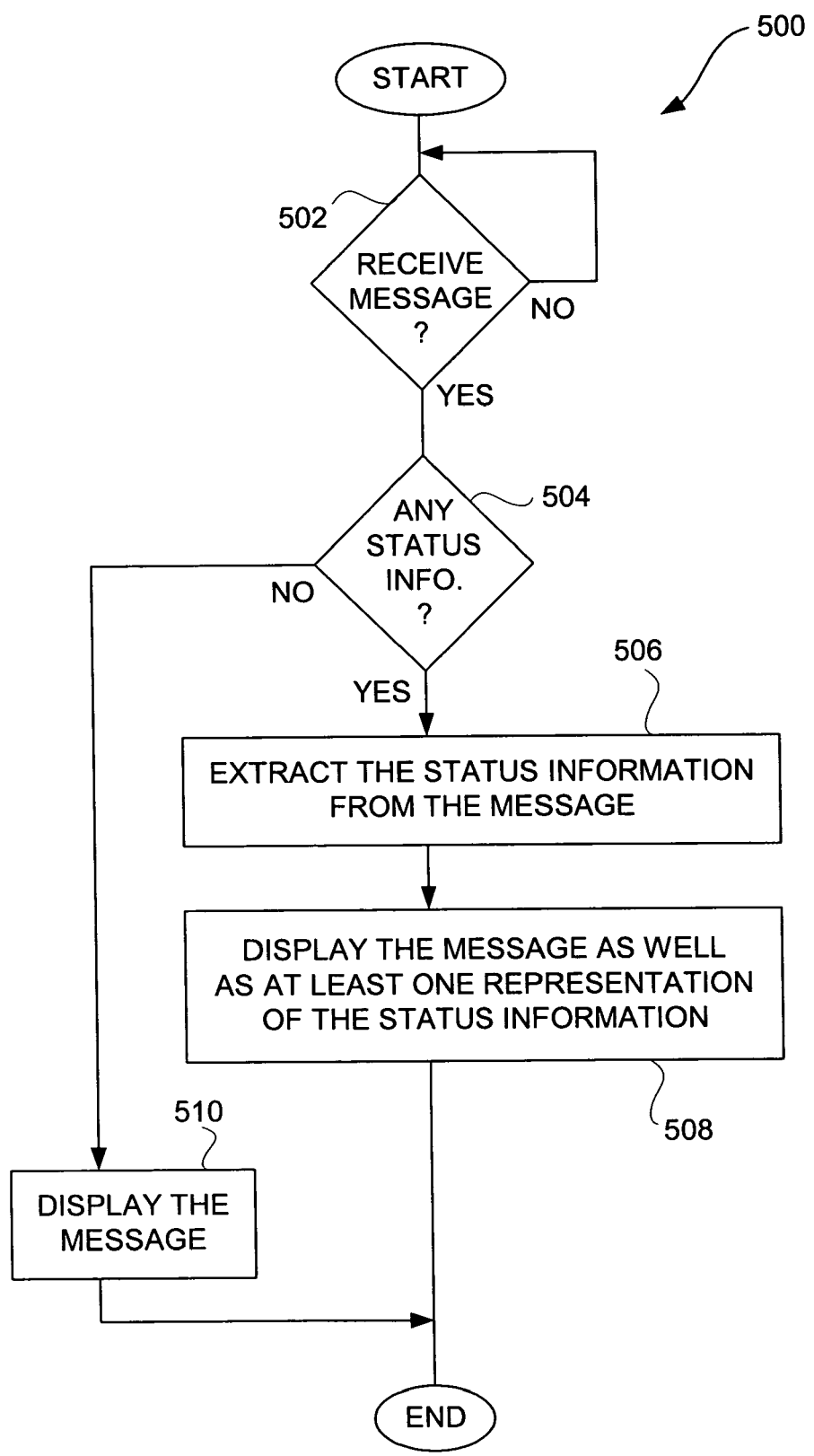
FIG. 5 is a flow diagram of display processing according to one embodiment of the invention.

FIG. 5 is a flow diagram of display processing 500 according to one embodiment of the invention. The display processing 500 is, for example, performed by a mobile communication device or other computing device. The display processing 500 is, for example, performed in response to a message being received due to the send processing 400 of FIG. 4. In other words, the display processing 500 can be performed by a computing device associated with a recipient that has received a message.

The display processing 500 begins with a decision 502 that determines whether a message has been received. When the decision 502 determines that a message has not yet been received, then the display processing 500 awaits the receipt of a message. On the other hand, when the decision 502 determines that a message has been received, a decision 504 then determines whether any status information is provided with the message that has been received. Here, the message is examined to determine whether status information is provided within the message. When the decision 504 determines that status information is provided with the message (and thus the message is an enhanced message), then the status information is extracted 506 from the message.

Next, the message as well as at least one representation of the status information are displayed 508. The representation (e.g., indication) of the status information being displayed can vary with implementation. In one embodiment, the representation is a graphical symbol that represents at least a portion of the status information. For example, a smiling face icon can represent a happy mood, a frown face icon can represent that the user is unhappy, etc. In another embodiment, the representation is textual information that is or represents a portion of the status information. In still another embodiment, the representation is a link (e.g., hyperlink) that provides access to at least a portion of the status information. For such representations, the status information can specify its presentation, or additional processing of the status information can determine an appropriate presentation.

The status information can also be interpreted, analyzed or processed before or while the representation to be displayed is determined. In one embodiment, such interpretation, analysis or processing can be performed, at least in part, by the device sending the message. As one example, the status information can include (or interpreted to include) temperature (e.g., ambient temperature) and user perspiration. Based on these two pieces of status information, one interpretation is that the user is perspiring (i.e., sweating) because of the high temperature.

As another example of the interpretation of status information, relative position of two computing devices can be computed and displayed. For example, if a receiving-computing device (either mobile or stationary) receives position information from a sending-computing device (preferably mobile), then the receiving-computing device (which knows its position) can determine and display the relative position (e.g., distance and/or direction) of the sending and the receiving-computing devices. Further, through use of other conditions information pertaining to the sending-computing device that might also be provided to the receiving-computing device, the receiving-computing device can also display the speed (velocity), direction of travel, etc. of the sending-computing device. Through additional interpretation or analysis of the conditions information, the speed (or average speed) could be used to categorize the type of movement of the sending-computing device, which would be available for display, as a symbol or other indication. As examples, the categories could be auto, bicycle, run, fast walk, slow walk, and stationary.

In yet another example, conditions information can include the user's mood. This can be measured in a number of different ways. One method is discussed in U.S. Pat. No. 5,774,591, entitled, "APPARATUS AND METHOD FOR RECOGNIZING FACIAL EXPRESSIONS AND FACIAL GESTURES IN A SEQUENCE OF IMAGES," which is hereby incorporated herein by reference. Such conditions information can be interpreted at the sending-computing device or the receiving-computing device. Conditions information can be a user's stress level. This piece of status information can, for example, be interpreted and transformed into a symbol, such as a stressed-face icon which the stress level is high. In one embodiment, both the raw data and the symbol(s) are transmitted to a receiving-computing device, but with only the symbol being displayed and the raw data being hidden. By selecting the displayed symbol or through other appropriate user-input, the receiving-computing device can additionally analyze or view the raw data.

Alternatively, when the decision 504 determines that status information is not provided with the message, then the message is displayed 510. Here, there is no status information available to present; therefore, the message is simply displayed. Following the operations 508 and 510, the display processing 500 is complete and ends.

The display processing 500 operates to present at least an indicator or representation of the status information through a display. In another embodiment, the status can be presented to the user of the mobile communication device or other computing device in other ways. For example, the status information could be presented by an audio output (e.g., synthesized voice), a tactile output or other types of outputs that can be sensed by the user, which is typically a living being, such as a human being.

In one aspect of the invention, status information can be automatically included with user-entered messages being sent as noted above. As another aspect of the invention, status information can be acquired and presented on request.

Figure 6:
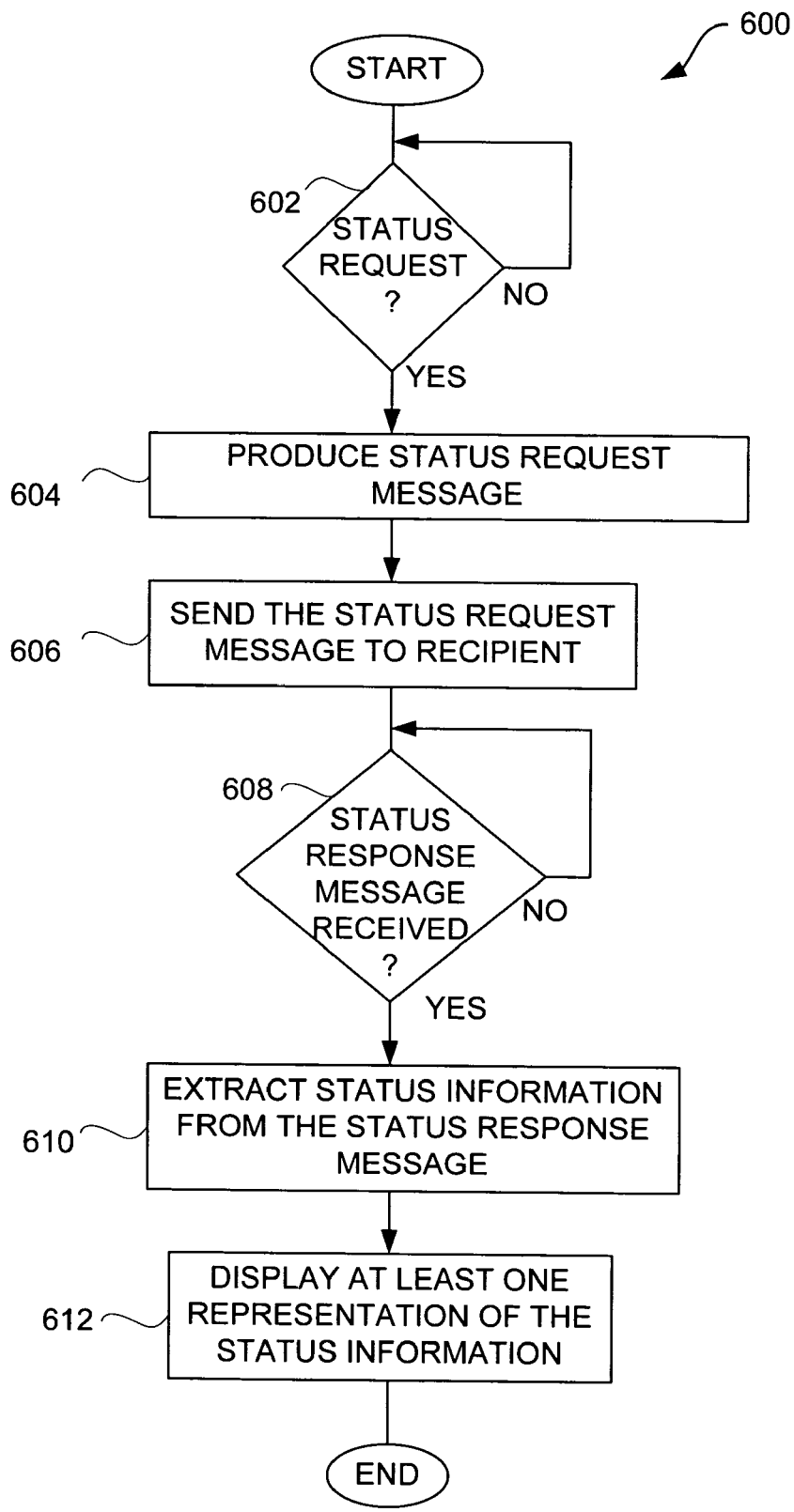
FIG. 6 is a flow diagram of status retrieval processing according to one embodiment of the invention.

FIG. 6 is a flow diagram of status retrieval processing 600 according to one embodiment of the invention. The status retrieval processing 600 is, for example, performed by a mobile communication device or other computing device.

The status retrieval processing 600 begins with a decision 602 that determines whether a status request has been requested. The status request is provided by a requestor to acquire status information from another mobile communication device or other computing device. In one embodiment, the status request is initiated by a requestor. The requestor can be a user of the mobile communication device or other computing device. In another embodiment, the status request can be initiated by the mobile communication device or other computing device. When the decision 602 determines that a status request has not been requested, then the status retrieval processing 600 awaits such a request.

Once the decision 602 determines that a status request has been requested, a status request message is produced 604. The status request message is then sent 606 from the requestor to a recipient. In one embodiment, the status request message is a short text message (e.g., SMS message) that need not be displayed at the recipient. A status request message that is not displayed at the recipient can be referred to as a dummy message. The recipient can be another mobile communication device or other computing device, or a user thereof.

Next, a decision 608 determines whether a status response message has been received by the requestor. The status response message includes status information associated with the recipient. The status response message is a message sent by the recipient in response to the status request message from the requestor. When the decision 608 determines that the status response message has not yet been received, then the status retrieval processing 600 awaits receipt of a status response message. On the other hand, when the decision 608 determines that a status response message (responsive to the status request message) has been received, then the status retrieval processing 600 continues. Namely, status information is extracted 610 from the status response message. Next, at least one representation of the status information is displayed 612. The representation can vary with implementation. In one embodiment, the representation is a graphical symbol that represents at least a portion of the status information. In another embodiment, the representation is text that is or represents a portion of the status information. In another embodiment, the representation is a piece of video clip that is or represents a portion of the status information. In still another embodiment, the representation is a link (e.g., hyperlink) that provides access to at least a portion of the status information. The status information can also be interpreted, analyzed or processed before or while the representation to be displayed is determined. Following the operation 600, the status retrieval processing 600 is complete and ends.

Figure 7:
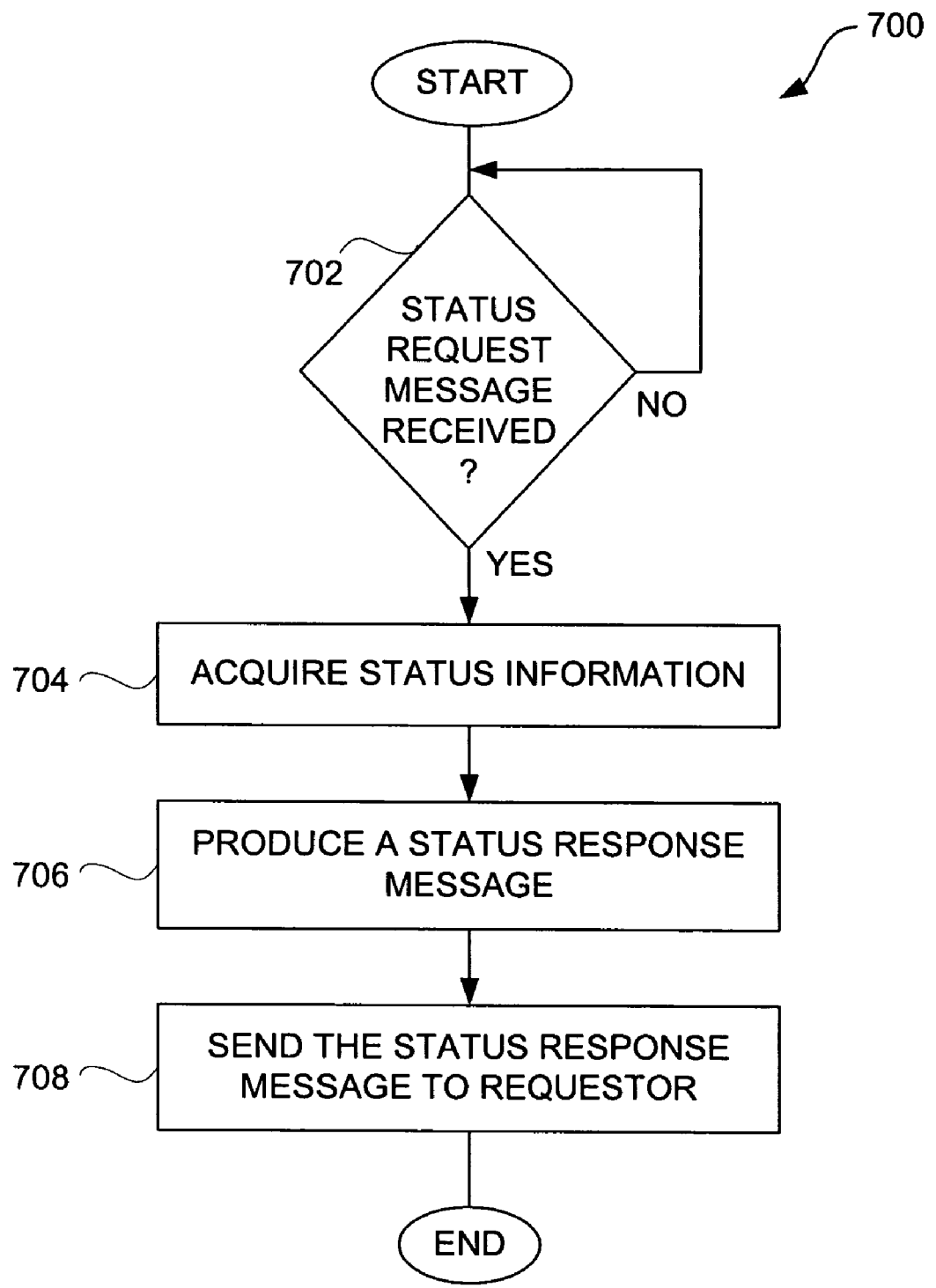
FIG. 7 is a flow diagram of status request processing according to one embodiment of the invention.

FIG. 7 is a flow diagram of status request processing 700 according to one embodiment of the invention. The status request processing 700 is, for example, performed by a mobile communication device or other computing device. The status request processing 700 is, for example, performed in response to a status request message of the status retrieval processing 600 of FIG. 6.

The status request processing 700 begins with a decision 702 that determines whether a status request message has been received. When the decision 702 determines that a status request message has not yet been received, then the status request processing 700 awaits such a message. Once the decision 702 determines that a status request message has been received, status information for the associated mobile communication device or other computing device or user thereof is acquired 704. A status response message is then produced 706 based on the status information. The status response message is then sent 708 to the requestor. The requestor can be considered to be a mobile communication device or other computing device, or a user thereof, that caused the status request message to be sent. According to one embodiment, once the status response message is sent 708, the operations 610-612 of the status retrieval processing 600 of FIG. 6 can be performed.

As described above, status information is typically presented in some manner at the recipient (often presented concurrently with a message). In other embodiments, the status information can be stored in a database for later utilization. The messages can be subsequently searched, sorted or otherwise processed.

In still another aspect of the invention, status information can be automatically sent to one or more recipients whenever available or when changed. For example, one such embodiment could have a mobile communication device periodically or on events (e.g., status events) send its status information to another computing device. As another example, status information could be automatically sent to another computing device when changed by more that a threshold amount. This would enable the another computing device to maintain awareness of up-to-date status information of the mobile communication device. Like other embodiments, this embodiment can operate in a peer-to-peer manner or in a centralized manner.

Note that status sensors do not have to be embedded in a mobile communication device. A status sensor can be physically detached, but electronically coupled to a communication device through a wireless link, such as based on the Bluetooth or Wi-Fi technologies. In yet another embodiment, a status sensor electronically couples to a communication device through a wire connection.

In yet another embodiment, the sending of status information can be through user-activation. In other words, although a piece of status information is acquired via a status sensor, its transmission to another electronic device can depend on a user's voluntary action, such as pushing a button.

One application of the invention is to provide the status information with messages, such as text messages and in particular near real-time text messages, such as instant messages. Hence, users of computing devices, namely, mobile communication devices, can exchange near real-time text messages and in doing so can also exchange status information. In some embodiments, the exchange of status information is achieved automatically, without user initiation.

The messages can be provided in a markup language format. The status information can be embedded or included in the messages also in a markup language. As examples, the markup language include HTML, HDML, WML, XML, etc. The messages and/or status information can also be provided in a programming language format, such as JAVA or C.

Another application of the invention is in the medical area. For example, a patient carries a mobile communication device with a position detector. He is also carrying one or more status sensors that can sense, for example, his body temperature, blood pressure, blood sugar or glucose level, blood oxygen, spirometry, ECG, heart rate, arrhythmias, brain wave, other sound wave measurable by a stethoscope, and/or body fat. The sensors can be non-invasive or invasive. Also, the sensor(s) can be coupled to the device is a wireless or wired manner. Such status information can be transmitted upon his command. In one embodiment, a patient's mobile communication device sends a message ("Very tired.") to an emergency clinic. It is an enhanced message that includes some of the patient's status information, such as his physical location and blood sugar level. In response, a specialist at the clinic sends one or more messages back, instructing the patient how to care for himself and/or controlling the release of insulin into the patient. In the mean time, the specialist can dispatch an ambulance to pick him up.

A number of embodiments have been described based on text messages. The present invention is also applicable to other types of messages, such as voice messages. In one embodiment, the message is provided with a voice call, and the mobile communication device is a mobile telephone (e.g., cell phone).

Also, a number of embodiments have been described regarding a device sending information to another device. In one embodiment, a device can broadcast enhanced messages to many devices.

In yet another embodiment, communication among devices can be monitored and charged by a third party. For example, the user of a communicating device can be billed depending on the amount of enhanced messages he has been sending or the amount or degree of enhancement to messages. In one embodiment, both the recipient and the sender of the enhanced messages are billed. In another embodiment, the more types of status messages included, the higher the bill. For example, enhanced messages with position, temperature and humidity information will cost more than enhanced messages with just position.

The various aspects can be used separately or in any combination.

The above-described system, methods and processes can be used together with other aspects of a monitoring system or mobile device, including the various aspects described in: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION SYSTEM, METHOD AND APPARATUS FOR ACQUIRING, PRESENTING, MANAGING AND USING POSITION INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

The invention can be implemented in software, hardware or a combination of hardware and software. The invention can also be embodied as computer readable code on a computer readable medium. The computer readable medium can be any data storage device that can store data which can thereafter be read by a computing device. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield one or more of the following advantages. One advantage is that status information is able to be obtained easily while exchanging electronic messages or otherwise through use of electronic messages. Another advantage of the invention is that messages are able to be enhanced with status information acquired by sensors. Still another advantage of the invention is that it can operate in a point-to-point or centralized manner to gather and present status information between computing devices (e.g., mobile communication devices).

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A method implemented by a computing device for communicating between users of mobile communication devices, said method comprising:

obtaining a message from a first mobile communication device to be delivered to a second mobile communication device;

acquiring status information of the first mobile communication device, the status information including at least position information associated with the first mobile communication device;

associating the status information to the message; and sending the message along with the status information of the first mobile communication device to the second mobile communication device, wherein the message is from a user of the first mobile communication device, and the message is to be delivered to another user via the second mobile communication device, and wherein the message contains content from the user of the first mobile communication device and the message is distinct from the status information.

2. A method as recited in claim 1, wherein said associating of the status information to the message attaches the status information to the message.

3. A method as recited in claim 1, wherein said associating of the status information to the message embeds the status information within the message.

4. A method as recited in claim 1, wherein the first mobile communication device is a first mobile telephone, and the second mobile communication device is a second mobile telephone.

5. A method as recited in claim 1, wherein the position information is acquired by a Global Positioning System (GPS) receiver within the first mobile communication device.

6. A method as recited in claim 1, wherein the message is a text message, and wherein the content of the text message includes text chosen by the user of the first mobile communication device.

7. A method as recited in claim 6, wherein the text message is a SMS message.

8. A method as recited in claim 1, wherein said method comprises:

displaying a graphical indication at the first mobile communication device that indicates whether the position information is being acquired.

9. A method implemented by a computing device for facilitating communication between users of mobile communication devices, said method comprising:

obtaining a message from a first mobile communication device to be delivered to a second mobile communication device;

acquiring status information of the first mobile communication device, the status information including at least position information associated with the first mobile communication device;

determining whether the second mobile communication device or a user thereof is authorized to obtain the status information of the first mobile communication device; and if said determining determines that the second mobile communication device or a user thereof is authorized to obtain the status information of the first mobile communication device, (i) associating the status information to the message, and (ii) sending the message along with the status information of the first mobile communication device to the second mobile communication device, wherein the message is from a user of the first mobile communication device, and the message is to be delivered to the user of the second mobile communication device via the second mobile communication device, and wherein the message contains text and the message is distinct from the status information.

10. A method as recited in claim 9, wherein if said determining determines that the second mobile communication device or a user thereof is not authorized to obtain the status information of the first mobile communication device, sending the message without the status information to the second mobile communication device.

11. A method as recited in claim 9, wherein the first mobile communication device has access to a list of authorized recipients that are authorized to obtain the status information of the first mobile communication device, and wherein said determining of whether the second mobile communication device or a user thereof is authorized to obtain the status information of the first mobile communication device comprises checking whether the second mobile communication device or a user thereof is on the list of authorized recipients.

12. A method as recited in claim 9, wherein said method comprises:

presenting a graphical user interface at the first mobile communication device to enable the user thereof to block the status information from being sent to the second mobile communication device with messages being sent to any recipients.

13. A method for displaying a message on a display for a user of a wireless communication device, said method comprising:

receiving a message from another wireless communication device over a network;

determining whether the message includes at least status information;

extracting the status information from the message when said determining determines that the message includes at least the status information; and displaying the message and at least one representation of the status information on the display following said extracting when said determining determines that the message includes at least the status information, wherein the message includes a user message from the another wireless communication device, wherein the user message contains text, and wherein the user message is different from the status information.

14. A method as recited in claim 13, wherein the status information includes at least a received position information associated with the another wireless communication device, and wherein said method further comprises:

determining, based on the received position information, a relative position of the another wireless communication device with respect to a position of the wireless communication device; and displaying an indication of the relative position on the wireless communication device.

15. A method as recited in claim 14, wherein the relative position includes at least a distance from the wireless communication device to the another wireless communication device.

16. A method as recited in claim 14, wherein the relative position includes at least a distance and a direction from the wireless communication device to the another wireless communication device.

17. A method as recited in claim 13, wherein movement of the another wireless communication device can be categorized into a type of movement, and wherein said method further comprises:
processing the status information to categorize the type of movement pertaining to the another wireless communication device.

18. A method as recited in claim 17, wherein said method further comprises:
displaying a graphical indication of the type of movement.

19. A method as recited in claim 13, wherein said displaying displays a graphical representation of the status information.

20. A method implemented by a computing device for facilitating communication between users of mobile communication devices, said method comprising:
obtaining a message from a first mobile communication device to be delivered to a plurality of other mobile communication devices;
acquiring status information of the first mobile communication device, the status information including at least position information associated with the first mobile communication device;
determining whether the plurality of other mobile communication devices or users thereof are authorized to obtain the status information of the first mobile communication device; and
if said determining determines that the plurality of other mobile communication devices or users thereof are authorized to obtain the status information of the first mobile communication device, broadcasting the message along with the status information of the first mobile communication device to each of the plurality of other mobile communication devices,
wherein the message is from a user of the first mobile communication device, and
wherein the message is distinct from the status information.

21. A method as recited in claim 20, wherein the message is a SMS message, and wherein the content of the SMS message includes text chosen by the user of the first mobile communication device.

22. A non-transitory computer readable medium including at least executable computer program code tangibly stored therein for displaying a message on a display for a user of a wireless communication device, said computer readable medium comprising:
computer program code for receiving a message from another wireless communication device over a network;
computer program code for determining whether the message includes at least status information;
computer program code for extracting the status information from the message when said computer program code for determining determines that the message includes at least the status information; and
computer program code for displaying the message and at least one representation of the status information on the display when said computer program code for determining determines that the message includes at least the status information,
wherein the message is received from the another wireless communication device, and wherein the message is different from the status information.

23. A non-transitory computer readable medium as recited in claim 22, wherein the message is for the user of the wireless communication device.

24. A non-transitory computer readable medium as recited in claim 22, wherein the message is based on at least one received user input at the another wireless computing device.

25. A non-transitory computer readable medium as recited in claim 22, wherein the message is provided via a user input device associated with the another computing device.

* * * * *